(12) United States Patent
Hommeltoft

(10) Patent No.: US 9,403,743 B1
(45) Date of Patent: Aug. 2, 2016

(54) ETHER LUBRICANT SYNTHESIS USING ELECTROLYTICALLY GENERATED ALCOHOLATE ANIONS

(71) Applicant: Sven Ivar Hommeltoft, Pleasant Hill, CA (US)

(72) Inventor: Sven Ivar Hommeltoft, Pleasant Hill, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 14/540,672

(22) Filed: Nov. 13, 2014

(51) Int. Cl.
*C07C 41/01* (2006.01)
*C25B 3/04* (2006.01)

(52) U.S. Cl.
CPC .. *C07C 41/01* (2013.01); *C25B 3/04* (2013.01)

(58) Field of Classification Search
CPC ....................................................... C07C 41/01
See application file for complete search history.

(56) References Cited

U.S. PATENT DOCUMENTS

| | | |
|---|---|---|
| 4,217,184 A | 8/1980 | Kuck et al. |
| 4,250,000 A | 2/1981 | Kuck et al. |
| 5,286,354 A | 2/1994 | Bard et al. |
| 7,074,972 B2 | 7/2006 | Maas et al. |
| 7,479,576 B1 | 1/2009 | Hassan et al. |

*Primary Examiner* — Brian J Davis
(74) *Attorney, Agent, or Firm* — Susan M. Abernathy

(57) ABSTRACT

Processes for producing long chain ethers from via alkoxides using fatty acid containing feedstocks. In an embodiment, a long chain ether may be prepared by reacting a long chain alkoxide with an alkyl halide. In another embodiment, a long chain ether may be prepared by reacting an alkoxide with a halide derivative of a long chain secondary alcohol. In an embodiment, a long chain alkoxide may be generated electrolytically by feeding the corresponding long chain alcohol to a suitable electrolytic cell. In another embodiment, a long chain alkoxide may be prepared by reacting a long chain alcohol with a light alkoxide. In an embodiment, the light alkoxide may be generated electrolytically from a volatile alcohol.

20 Claims, 1 Drawing Sheet

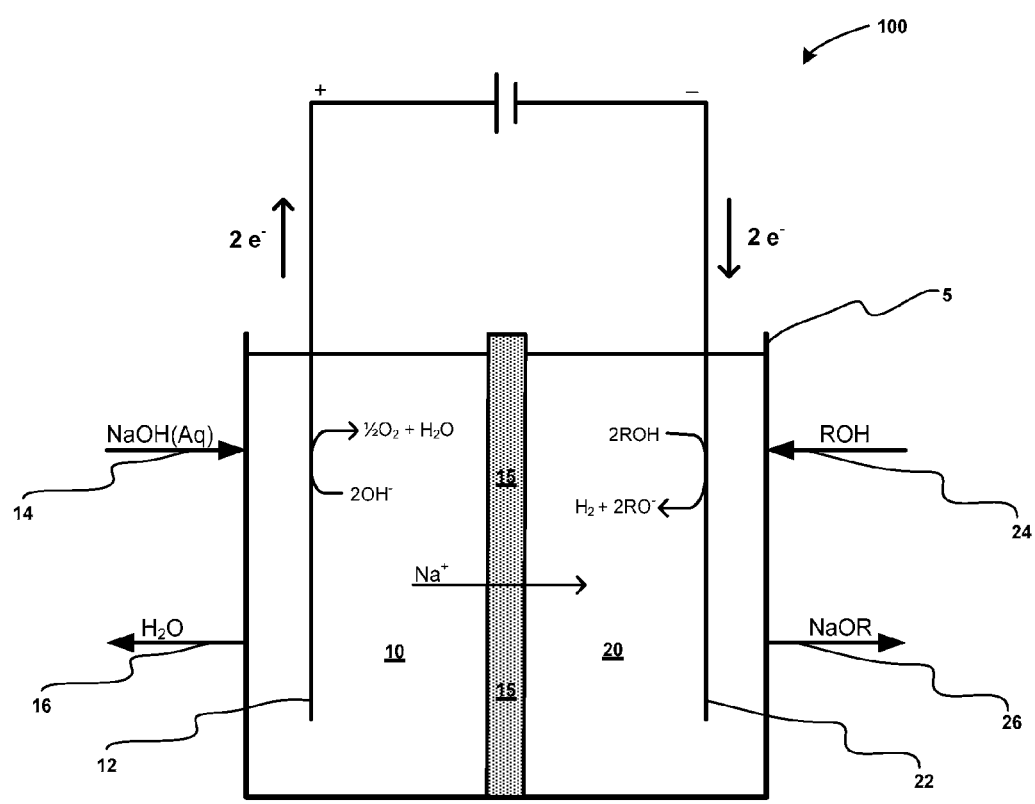

ETHER LUBRICANT SYNTHESIS USING ELECTROLYTICALLY GENERATED ALCOHOLATE ANIONS

TECHNICAL FIELD

This disclosure relates to processes for ether lubricant synthesis using alcoholate anions that may be electrolytically generated.

BACKGROUND

Some phenyl ethers have in the past been used as lubricants, but these typically have fairly high pour points and are not generally applied.

There is a need for long chain ether lubricants and for processes for efficiently producing long chain ether lubricants.

SUMMARY

In an embodiment there is provided a process comprising providing a long chain secondary alcohol having the following general Formula I:

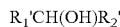  I wherein $R_1'$ and $R_2'$ are independently selected from the group consisting of $C_5$-$C_{21}$ linear or branched alkyl and $C_5$-$C_{21}$ linear or branched alkenyl, converting the long chain secondary alcohol to a long chain alkoxide corresponding to the long chain secondary alcohol, and reacting the long chain alkoxide with an alkylating agent to form a long chain ether according to the following Scheme 8:

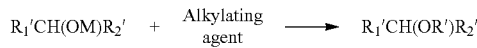

wherein M is an alkali metal, and R' is selected from the group consisting of $C_1$-$C_3$ alkyl, $C_4$-$C_{22}$ linear or branched alkyl, $C_2$-$C_3$ alkenyl, and $C_4$-$C_{22}$ linear or branched alkenyl.

In another embodiment there is provided a process comprising contacting at least one fatty acid with a ketonization catalyst in a ketonization zone under ketonization conditions to provide a long chain ketone according to the following Scheme 1:

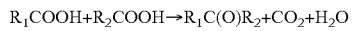

wherein $R_1$ and $R_2$ are independently selected from the group consisting of $C_5$-$C_{21}$ linear or branched alkyl and $C_5$-$C_{21}$ linear or branched alkenyl; and contacting the long chain ketone with a selective ketone hydrogenation catalyst in a ketone hydrogenation zone in the presence of hydrogen gas under selective ketone hydrogenation conditions to provide a long chain secondary alcohol according to the following Scheme 2:

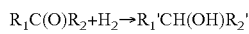

wherein $R_1$ and $R_2$ are the same or different, when $R_1$ is alkyl $R_1'=R_1$, when $R_2$ is alkyl $R_2'=R_2$, when $R_1$ is alkenyl $R_1'$ is alkyl or alkenyl, when $R_2$ is alkenyl $R_2'$ is alkyl or alkenyl, $R_1$ and $R_1'$ have an equal number of carbon atoms, and $R_2$ and $R_2'$ have an equal number of carbon atoms. The process further comprises converting the long chain secondary alcohol to a long chain alkoxide corresponding to the long chain secondary alcohol, and reacting the long chain alkoxide with an alkylating agent to form a long chain ether according to the following Scheme 8:

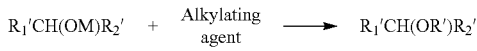

wherein M is an alkali metal, and R' is selected from the group consisting of $C_1$-$C_3$ alkyl, $C_4$-$C_{22}$ linear or branched alkyl, $C_2$-$C_3$ alkenyl, and $C_4$-$C_{22}$ linear or branched alkenyl.

In a further embodiment there is provided a process comprising contacting at least one fatty acid with a ketonization catalyst in a ketonization zone under ketonization conditions to provide a long chain ketone according to the following Scheme 1:

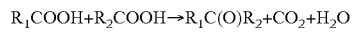

wherein $R_1$ and $R_2$ are independently selected from the group consisting of $C_5$-$C_{21}$ linear or branched alkyl and $C_5$-$C_{21}$ linear or branched alkenyl, and contacting the long chain ketone with a selective ketone hydrogenation catalyst in a ketone hydrogenation zone in the presence of hydrogen gas under selective ketone hydrogenation conditions to provide a first long chain secondary alcohol according to the following Scheme 2:

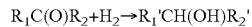

wherein $R_1$ and $R_2$ are the same or different, when $R_1$ is alkyl $R_1'=R_1$, when $R_2$ is alkyl $R_2'=R_2$, when $R_1$ is alkenyl $R_1'$ is alkyl or alkenyl, when $R_2$ is alkenyl $R_2'$ is alkyl or alkenyl, $R_1$ and $R_1'$ have an equal number of carbon atoms, and $R_2$ and $R_2'$ have an equal number of carbon atoms. The process further comprises reacting the first long chain secondary alcohol with a halogenating agent to form a halide derivative of the first long chain secondary alcohol according to the following Scheme 7A:

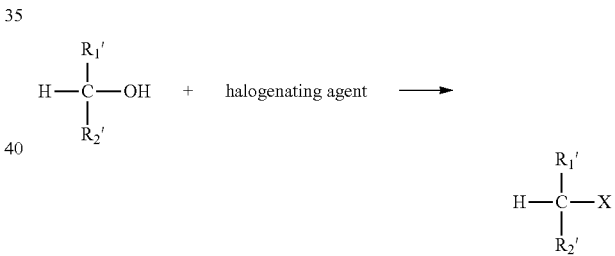

wherein X is a halogen atom. The process still further comprises providing a second alcohol, converting the second alcohol to an alkoxide corresponding to the second alcohol, and reacting the halide derivative of the first long chain secondary alcohol with the alkoxide to form a long chain ether.

BRIEF DESCRIPTION OF THE DRAWING

FIG. 1 schematically represents an electrolytic cell and process for electrolytically generating an alkoxide from an alcohol, according to an embodiment of the present invention.

DETAILED DESCRIPTION

Conventional processes for preparing alcohols with a carbon chain length above that of available fatty acids are expensive. Also, such conventional processes place the alcohol group toward the end of the molecule. Also, for lubricant applications it may be important to prepare molecules with a sufficiently high boiling point and viscosity to meet specifications for most lubricant products. This typically requires carbon chains considerably longer than the $C_{16}$-$C_{18}$ chains that are made simply by hydrogenation of the most commonly available fatty acids and fatty oil feedstocks.

Applicant has demonstrated a new route to make long chain secondary alcohols, from fatty acids and fatty oils, in which the OH group may be placed non-terminally in the molecule and in which the carbon chain length is about twice (2×) the length of the carbon chain of alcohols prepared by simple hydrogenation of fatty acids and fatty oils. Furthermore, Applicant has discovered that long chain ethers may be prepared from the long chain secondary alcohols via a number of different routes.

In an embodiment, a long chain ether may be prepared by reacting a long chain alkoxide with an alkyl halide. In another embodiment, a long chain ether may be prepared by reacting a long chain secondary alcohol with a halogenating agent to form a halide derivative of the first long chain secondary alcohol, and thereafter reacting the halide derivative with an alkoxide corresponding to a second alcohol. In an embodiment, alkoxides for use in preparing long chain ethers may be electrolytically generated. Long chain ethers produced as disclosed herein may find applications as lubricants.

Catalysts for Ketonization

In an embodiment, a suitable catalyst for ketonization may comprise alumina. In an embodiment, the ketonization catalyst may comprise at least 95 wt %, at least 99 wt %, or at least 99.5 wt % alumina. In an embodiment, the fresh ketonization catalyst may be calcined at a temperature in the range from 700 to 1100° F. (371 to 593° C.) for a time period in the range from 0.5 to 24 hours prior to contacting the ketonization catalyst with a reactant (long chain carboxylic acid or fatty acid). In an embodiment, the fresh ketonization catalyst may be calcined in the presence of steam. In an embodiment, the ketonization catalyst may comprise gamma alumina. In an embodiment, the ketonization catalyst may consist essentially of alumina.

In an embodiment, the surface area of the alumina catalyst for ketonization may be in the range from 15 to 500 m²/g of catalyst, or from 50 to 400 m²/g of catalyst, or from 100 to 250 m²/g of catalyst. In an embodiment, an alumina catalyst useful for ketonization reactions as disclosed herein may have various shapes including, for example, granules, pellets, spheres, extrudates, and the like. The alumina catalyst may be disposed within a ketonization zone. A ketonization zone is not limited to any particular reactor type. For example, a ketonization zone may use a fixed-, fluidized-, or moving bed reactor.

Over time, the ketonization catalyst may passivate and lose activity. An alumina catalyst that has become passivated to varying degrees following ketonization may be regenerated, e.g., as described in commonly assigned U.S. patent application Ser. No. 14/540,723 filed herewith and entitled Ketonization process using oxidative catalyst regeneration.

Fatty Acid Ketonization

A ketone product may be prepared by contacting at least one fatty acid with a ketonization catalyst in a ketonization zone under ketonization conditions according to the following scheme (Scheme 1), wherein $R_1$ and $R_2$ are saturated or unsaturated aliphatic groups, and wherein $R_1$ and $R_2$ may be the same or different. As a non-limiting example, $R_1$ and $R_2$ may be independently selected from $C_5$-$C_{21}$ linear or branched alkyl and $C_5$-$C_{21}$ linear or branched alkenyl.

Scheme 1:

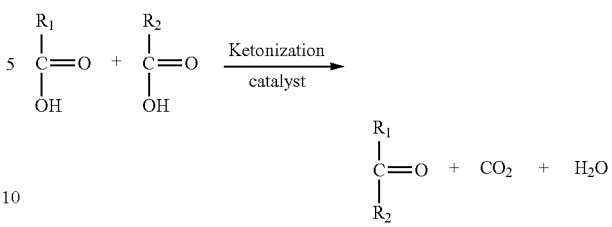

In a sub-embodiment, $R_1$ and $R_2$ may be independently selected from $C_7$-$C_{17}$ linear or branched alkyl or alkenyl, or from $C_9$-$C_{17}$ linear or branched alkyl or alkenyl, or from $C_9$-$C_{15}$ linear or branched alkyl or alkenyl, or from $C_{15}$-$C_{17}$ linear or branched alkyl or alkenyl. In an embodiment, ketonization may also be known as ketonic decarboxylation or fatty acid decarboxylation-coupling.

In an embodiment, the step of contacting the at least one fatty acid with the ketonization catalyst may comprise feeding a feedstock comprising the at least one fatty acid to the ketonization zone. In an embodiment, feedstocks for ketonization as disclosed herein may be derived from a triglyceride-containing biomass source such as oils or fats from plants and/or animals. In an embodiment, the feedstock may be obtained from biological material (e.g., fatty biomass) having a lipid content greater than (>) 30 wt % on a dry weight basis, or >50, or >70, or >90, or >95, or >99 wt % on a dry weight basis. In an embodiment, the biological material may comprises vegetable oil, animal tallow, algae, and combinations thereof. In an embodiment, the fatty acid feedstock may be derived from other, non-biomass, sources (e.g., Fischer-Tropsch synthesis). Such alternatively derived fatty acids may be mixed or blended with biomass derived fatty acids prior to ketonization, e.g., to alleviate logistical and/or supply related issues involving biomass.

In an embodiment, feedstocks for ketonization may comprise at least one fatty acid reactant or a mixture of fatty acid reactants. In an embodiment, the at least one fatty acid reactant for ketonization may comprise a mixture of at least two (2) fatty acids. In an embodiment, reactants for ketonization may comprise $C_6$-$C_{22}$ fatty acids and/or $C_6$-$C_{22}$ fatty acid derivatives. In an embodiment, such fatty acid derivatives may include $C_6$-$C_{22}$ fatty acid mono-, di-, and triglycerides, $C_6$-$C_{22}$ acyl halides, and $C_6$-$C_{22}$ salts of fatty acids. In a sub-embodiment, the fatty acids and/or fatty acid derivatives for ketonization may be in the range from $C_8$-$C_{18}$, or in the range from $C_{16}$-$C_{18}$. In an embodiment, at least one fatty acid for ketonization may be obtained from biological material, including various organisms and biological systems. In an embodiment, the at least one fatty acid may be obtained from at least one naturally occurring triglyceride, for example, wherein the triglyceride may be obtained from biomass. In an embodiment, feedstocks for ketonization may comprise at least 95 wt % fatty acids or at least 99 wt % fatty acids.

In an embodiment, reactants for ketonization may be derived from one or more triglyceride-containing vegetable oils such as, but not limited to, coconut oil, corn oil, linseed oil, olive oil, palm oil, palm kernel oil, rapeseed oil, safflower oil, soybean oil, sunflower oil, and the like. Additional or alternative sources of triglycerides, which can be hydrolyzed to yield fatty acids, include, but are not limited to, algae, animal tallow, and zooplankton.

In an embodiment, reactants for ketonization may include, without limitation, $C_8$-$C_{22}$ fatty acids, and combinations thereof. Examples of suitable saturated fatty acids may include, without limitation, caproic acid ($C_6$), caprylic acid ($C_8$), capric acid ($C_{10}$), lauric acid ($C_{12}$), myristic acid ($C_{14}$), palmitic acid ($C_{16}$), stearic acid ($C_{18}$), eicosanoic acid ($C_{20}$).

Examples of unsaturated fatty acids may include, without limitation, palmitoleic acid, oleic acid, and linoleic acid. Reactants for ketonization may further include, without limitation, palm kernel oil, palm oil, coconut oil, corn oil, soy bean oil, rape seed (canola) oil, poultry fat, beef tallow, and their respective fatty acid constituents, and combinations thereof.

In an embodiment, the reactants for the ketonization reaction or step may be hydrogenated to substantially saturate some or all of the double bonds prior to ketonization. In cases where the fatty oils, i.e. triglycerides, are hydrolyzed to fatty acids, such saturation of the double bonds may be done before or after the hydrolysis.

In some aspects, wherein the above-mentioned hydrolyzed triglyceride sources contain mixtures of saturated fatty acids, mono-unsaturated fatty acids, and polyunsaturated fatty acids, one or more techniques may be employed to isolate, concentrate, or otherwise separate one or more types of fatty acids from one or more other types of fatty acids in the mixture (see, e.g., U.S. Pat. No. 8,097,740 to Miller).

Prior to contacting the reactant with the ketonization catalyst in the ketonization zone, the ketonization catalyst may be calcined. In an embodiment, the step of calcining the ketonization catalyst may be performed in the presence of steam. In an embodiment, the step of calcining the ketonization catalyst may be performed at a temperature in the range from 400 to 600° C., or from 450 to 500° C., for a time period in the range from 0.5 to 10 hours, or from 1 to 2 hours.

In an embodiment, a suitable catalyst for fatty acid ketonization may comprise alumina. In an embodiment, the ketonization catalyst may comprise substantially pure gamma alumina. In an embodiment, the ketonization catalyst may consist essentially of alumina.

Suitable ketonization conditions may include a temperature in the range from 100 to 500° C., or from 300 to 450° C.; a pressure in the range from 0.5 to 100 psi, or from 5 to 30 psi; and a liquid hourly space velocity (LHSV) in the range from 0.1 to 50 h$^-$, or from 0.5 to 10 h$^{-1}$. In an embodiment, the partial pressure of the fatty acid in the ketonization zone may be maintained in the range of 0.1 to 30 psi. The ketonization process can be carried out in batch or continuous mode, with recycling of unconsumed starting materials if required.

In an embodiment, the decarboxylation reaction may be conducted in the presence of at least one gaseous- or liquid feedstock diluent. In an embodiment, the ketonization reaction may be carried out while the fatty acid is maintained in the vapor phase. Conditions for fatty acid ketonization are disclosed in commonly assigned U.S. patent application Ser. No. 13/486,097, filed Jun. 1, 2012, entitled Process for producing ketones from fatty acids. In an embodiment, a fatty acid reactant for the ketonization reaction may comprises a mixture of at least two (2) fatty acids such that the ketone product may comprise a mixture of at least three (3) different long chain ketones, each of which may be selectively hydrogenated to provide a mixture of at least three (3) different long chain secondary alcohols.

In an embodiment, the long chain ketones provided by the ketonization reaction can be separated from by-products (such as oligomeric or polymeric species and low molecular weight "fragments" from the fatty acid chains) by distillation. For example, in an embodiment the crude reaction product can be subjected to a distillation-separation at atmospheric or reduced pressure through a packed distillation column. In an embodiment, the ketonization product may be a wax under ambient conditions.

The long chain ketones produced from fatty acids, e.g., as disclosed hereinabove, may be converted to their corresponding long chain secondary alcohol by selective ketone hydrogenation over a selective ketone hydrogenation catalyst, e.g., as disclosed hereinbelow.

Catalysts for Selective Ketone Hydrogenation

A catalyst for the selective hydrogenation of long chain ketones to the corresponding secondary alcohols may be referred to herein as a "selective ketone hydrogenation catalyst." In an embodiment, the selective ketone hydrogenation catalyst for selective hydrogenation of long chain (e.g., $C_{11}$+) ketones may comprise a metal selected from Pt, Pd, Ru, Ni, Co, Mo, Cr, Cu, Rh, and combinations thereof. In an embodiment, the selective ketone hydrogenation catalyst may further comprise a support material. In an embodiment, the support material may be selected from carbon, silica, magnesia, titania, and combinations thereof. In an embodiment, at least some metal component(s) of the hydrogenation catalyst may be in elemental form. As a non-limiting example, the hydrogenation catalyst may comprise a metal selected from Pt, Pd, Ru, Ni, Rh, and combinations thereof, and the metal may be in elemental form in the hydrogenation catalyst. In a sub-embodiment, the hydrogenation catalyst may comprise a metal selected from Pt, Pd, and combinations thereof, and a support material comprising carbon, silica, magnesia, titania, and combinations thereof. In an embodiment, the hydrogenation catalyst may be unsupported meaning, for example, that the metal may be present either in finely divided form (e.g., as metal powder) or in pelletized or extruded or other structural form without the presence of a support material.

In an embodiment, the selective ketone hydrogenation catalyst lacks, or is devoid of, any component that promotes the dehydration of alcohols, such that the hydrogenation catalyst as a whole lacks catalytic activity for dehydration of the long chain secondary alcohol, under the conditions used for the selective hydrogenation of long chain ketones, such that ketone conversion to the corresponding alkene or alkane is prevented. Because the long chain ketones as disclosed herein exhibit comparatively low reactivity in the ketone hydrogenation reaction, e.g., in comparison with $C_3$ or $C_4$ ketones, more forcing conditions may be required for hydrogenation as compared to hydrogenation of lighter ketones; such (more forcing) conditions would be expected to exacerbate the negative effect on product selectivity of a hydrogenation catalyst having dehydration functionality. This highlights the significance of using a selective ketone hydrogenation catalyst, in processes as disclosed herein, for the efficient conversion of long chain ketones to the corresponding long chain secondary alcohols in high yield.

In an embodiment, a selective ketone hydrogenation catalyst will lack alumina. As an example, the selective ketone hydrogenation catalyst may be prepared without the use of an alumina component and with a support material, if any, lacking an alumina component, such that the selective ketone hydrogenation catalyst contains at most only trace amounts of alumina that are insufficient to be catalytically effective in dehydrating long chain secondary alcohols under the hydrogenation conditions as disclosed herein for the selective hydrogenation of long chain ketones to the corresponding secondary alcohols.

This is in stark contrast to conventional hydrotreating catalysts having alumina support material that is the major catalyst component by weight and volume. Applicant has observed that the presence of alumina, e.g., in conventional hydrotreating catalysts, negatively impacts the conversion of long chain ketones to the corresponding secondary alcohol product(s) as disclosed herein.

In an embodiment, the surface area of the hydrogenation catalyst may be in the range from 15 to 1000 m²/g of catalyst, or from 100 to 600 m²/g of catalyst, or from 250 to 450 m²/g of catalyst. In an embodiment a selective ketone hydrogenation catalyst, useful for selective hydrogenation of long chain ketones as disclosed herein, may have various shapes including, for example, powder, granules, pellets, spheres, extrudates, and the like. The selective ketone hydrogenation catalyst may be disposed within a ketone hydrogenation zone or ketone hydrogenation reactor. The ketone hydrogenation zone is not limited to any particular reactor type.

Long Chain Secondary Alcohols by Selective Hydrogenation of Long Chain Ketones

As described hereinabove, a long chain ketone may be prepared, e.g., according to Scheme 1 by contacting at least one fatty acid with a ketonization catalyst in a ketonization zone under ketonization conditions. The long chain ketone may then be selectively hydrogenated by contacting the long chain ketone with a selective ketone hydrogenation catalyst in a ketone hydrogenation zone under selective ketone hydrogenation conditions according to the following Scheme 2 to provide a long chain secondary alcohol.

Scheme 2:

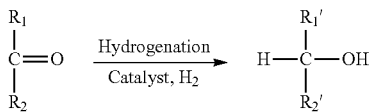

In Schemes 1 and 2, $R_1$ and $R_2$ may be the same or different, $R_1$ and $R_2$ may be independently selected from $C_5$-$C_{21}$ linear or branched alkyl and $C_5$-$C_{21}$ linear or branched alkenyl, wherein: when $R_1$ is alkyl $R_1'$=$R_1$, when $R_2$ is alkyl $R_2'$=$R_2$, when $R_1$ is alkenyl $R_1'$ is alkyl or alkenyl, when $R_2$ is alkenyl $R_2'$ is alkyl or alkenyl, and wherein $R_1$ and $R_1'$ have an equal number of carbon atoms, and $R_2$ and $R_2'$ have an equal number of carbon atoms. In an embodiment, $R_1'$ and $R_2'$ may be independently selected from $C_7$-$C_{17}$ linear or branched alkyl, or from $C_9$-$C_{17}$ linear or branched alkyl, or from $C_9$-$C_{15}$ linear or branched alkyl, or from $C_{15}$-$C_{17}$ linear or branched alkyl.

While not being bound by theory, in an embodiment wherein $R_1$ and $R_2$ are alkenyl, the product alcohol may be the corresponding saturated alcohol, since alkenyl group hydrogenation is typically more *facile* than ketone hydrogenation. As an example, when $R_1$ is alkenyl $R_1'$ may be alkyl, and when $R_2$ is alkenyl $R_2'$ may be alkyl. In a sub-embodiment, $R_1'$ and $R_2'$ may be independently selected from the group consisting of $C_5$-$C_{21}$ linear or branched alkyl.

In an embodiment, the at least one fatty acid may comprise a mixture of at least two (2) fatty acids, such that the long chain ketone prepared according to Scheme 1 may comprise a mixture of at least three (3) different long chain ketones, and the long chain secondary alcohol prepared according to Scheme 2 may similarly comprise a mixture of at least three (3) different long chain secondary alcohols.

In an embodiment, the selective ketone hydrogenation catalyst will lack catalytic activity for dehydration of the long chain secondary alcohol under the selective ketone hydrogenation conditions used such that, during the step of contacting the long chain ketone with the selective ketone hydrogenation catalyst, ketone conversion to the corresponding alkene or alkane is prevented or hindered. As a result, the corresponding secondary alcohol may be obtained from the long chain ketone with excellent selectivity (e.g., >80% selectivity at 90% conversion).

In an embodiment, a process for preparing long chain secondary alcohols may comprise avoiding contact of the at least one long chain ketone with alumina during the selective ketone hydrogenation step. For example, alumina promotes alcohol dehydration to alkenes, which may in turn be converted to alkanes during conventional hydrogenation, thereby substantially or greatly decreasing the yield of long chain secondary alcohols. Accordingly in an embodiment, the selective ketone hydrogenation catalyst as disclosed herein may be prepared without the use of alumina. In an embodiment, alumina or other material(s) that promote(s) alcohol dehydration may be specifically excluded from the selective ketone hydrogenation catalyst and the ketone hydrogenation zone.

In an embodiment, the selective ketone hydrogenation catalyst may comprise a metal selected from Pt, Pd, Ru, Ni, Co, Mo, Cr, Cu, Rh, and combinations thereof. In an embodiment, the hydrogenation catalyst may further comprise a support material selected from carbon, silica, magnesia, titania, and combinations thereof. In a sub-embodiment, the hydrogenation catalyst may comprise a metal selected from the group consisting of Pt, Pd, and combinations thereof, and a support material selected from carbon, silica, magnesia, titania, and combinations thereof.

In an embodiment, the ketone hydrogenation step may be performed in the absence of a material that promotes dehydration of the long chain secondary alcohol under the selective ketone hydrogenation conditions used, so as to prevent or hinder ketone conversion to the corresponding alkene or alkane, in order to greatly increase the selectivity of ketone conversion to the long chain secondary alcohol product. As a non-limiting example, the selective ketone hydrogenation step may be performed in the absence of alumina. Alumina is used as a catalyst support in conventional hydrotreating catalysts; however, processes as disclosed herein may involve avoiding the presence of alumina during ketone hydrogenation for the production of long chain secondary alcohols. In an embodiment, alumina may be avoided during the ketone hydrogenation step by using a selective ketone hydrogenation catalyst that lacks an alumina component. Selective ketone hydrogenation catalysts that lack alumina are described hereinabove.

In an embodiment, the selectivity of long chain ketone conversion to the corresponding long chain secondary alcohol via the selective ketone hydrogenation step (e.g., according to Scheme 2) may be much higher, e.g., typically at least about 15% higher, than that of comparable ketone hydrogenation in the presence of a conventional hydrotreating catalyst comprising alumina. As a non-limiting example, the selectivity of ketone conversion to the corresponding long chain secondary alcohol by a selective ketone hydrogenation catalyst as disclosed herein may be greater than (>) 80% at 90% conversion, whereas the selectivity of ketone conversion to the corresponding long chain secondary alcohol by a conventional hydrogenation catalyst comprising an alumina support is typically less than (<) 70% at 90% conversion.

In an embodiment, $R_1$ and $R_2$ in Schemes 1 and 2 may each be linear or branched alkyl. In a sub-embodiment, $R_1$ and $R_2$ may be independently selected from $C_5$-$C_{21}$ linear or branched alkyl, or from $C_7$-$C_{17}$ linear or branched alkyl, or from $C_9$-$C_{17}$ linear or branched alkyl, or from $C_9$-$C_{15}$ linear or branched alkyl, or from $C_{15}$-$C_{17}$ linear or branched alkyl. In an embodiment, the at least one long chain secondary alcohol formed by ketone hydrogenation, e.g., according to Scheme 2, may be in the range from $C_{11}$-$C_{43}$, or from $C_{21}$-$C_{31}$, or from $C_{31}$-$C_{35}$. In an embodiment, long chain secondary alcohols prepared by processes as disclosed herein may comprise a mixture of long chain secondary alcohols, e.g., each having from 11 to 43 carbon atoms per molecule. In an embodiment, each of the long chain secondary alcohols may have the hydroxyl group placed at a non-terminal location of the molecule. In a further embodiment, a long chain secondary alcohol prepared according to embodiments of processes disclosed herein may have the OH group placed at- or near the center of the secondary alcohol molecule.

In an embodiment, fatty acid ketonization may comprise contacting a mixture of at least two (2) fatty acids with the ketonization catalyst in the ketonization zone. In an embodiment, such a mixture of fatty acids may comprise a lipid mixture derived from a source of lipids selected from a plant, an animal, or other organism(s). Such sources of lipids may include, without limitation, terrestrial plants, mammals, microorganisms, aquatic plants, seaweed, algae, phytoplankton, and the like. In an embodiment, a mixture of fatty acids for ketonization according to processes as disclosed herein may be derived from palm kernel oil, palm oil, coconut oil, corn oil, soy bean oil, rape seed (canola) oil, poultry fat, beef tallow, and the like and their respective fatty acid constituents, and combinations thereof.

In another embodiment, a process for preparing a long chain secondary alcohol may comprise reacting a first fatty acid with a second fatty acid to form a long chain ketone, and selectively hydrogenating the long chain ketone to selectively form the corresponding secondary alcohol.

In an embodiment, the selectively hydrogenating step may comprise contacting the long chain ketone with a selective ketone hydrogenation catalyst in a ketone hydrogenation zone under selective ketone hydrogenation conditions. In an embodiment, the selective ketone hydrogenation catalyst will lack catalytic activity for dehydration of the secondary alcohol, under the selective ketone hydrogenation conditions used, such that ketone conversion to the corresponding alkene or alkane is prevented. Due to the relatively low reactivity of long chain ketones (e.g., $C_{11}$-$C_{43}$) in the ketone hydrogenation reaction, as compared with lighter ketones (e.g., $C_3$ or $C_4$), the more forcing conditions used for the long chain ketones would exacerbate the negative effect that a hydrogenation catalyst having dehydration functionality would have on product selectivity. Instead, the use of a selective ketone hydrogenation catalyst that at least substantially lacks dehydration activity, as disclosed herein, allows for the efficient conversion of long chain ketones with high selectivity to the corresponding long chain secondary alcohols.

In an embodiment, exemplary conditions for selective ketone hydrogenation may comprise a temperature in the range from 200 to 755° F. (93 to 402° C.), or from 355 to 755° F. (179 to 402° C.), or from 400 to 750° F. (204 to 399° C.), a pressure in the range from 200 to 5000 psi, or from 250 to 5000 psi, or from 300 to 4000 psi, a liquid hourly space velocity (LHSV) in the range from 0.05 to 5.0 h$^{-1}$, or from 0.1 to 5.0 h$^{-1}$, or from 0.5 to 4.0 h$^{-1}$, and a hydrogen to feed molar ratio in the range from 1.0 to 1000, or from 5.0 to 1000, or from 10 to 1000. In an embodiment, the hydrogenation catalyst may comprise a metal selected from the group consisting of Pt, Pd, Ru, Ni, Co, Mo, Cr, Cu, Rh, and combinations thereof. In a sub-embodiment, the metal may be selected from Pt, Pd, and combinations thereof.

As described hereinabove, the selective hydrogenation of long chain ketones may be performed in the absence of a material that promotes dehydration of the secondary alcohol under selective ketone hydrogenation conditions, such that conversion to the corresponding alkene or alkane is prevented or hindered. Accordingly, the selective ketone hydrogenation catalyst will lack a material, such as alumina, that promotes dehydration of the secondary alcohol under said selective ketone hydrogenation conditions. This is in contrast to conventional hydrotreating catalysts having an alumina support that promotes alcohol dehydration to alkenes, with subsequent hydrogenation to alkanes. Advantageously, selective ketone hydrogenation as disclosed herein allows the corresponding secondary alcohol to be obtained efficiently with excellent selectivity.

In an embodiment, long chain secondary alcohol product(s) prepared as disclosed herein may comprise a mixture of long chain secondary alcohols and may be subjected to various separation processes. Such separation may involve, for example, distilling and/or flash distillation to provide one or more long chain secondary alcohol products.

Long Chain Ethers Prepared from Long Chain Secondary Alcohols

In an embodiment, a process for preparing a long chain ether may comprise providing a long chain ketone, e.g., via fatty acid ketonization as described hereinabove according to Scheme 1, supra, and thereafter contacting the long chain ketone with a selective ketone hydrogenation catalyst under selective ketone hydrogenation conditions, e.g., as described hereinabove, to provide a long chain secondary alcohol according to the following Scheme 2:

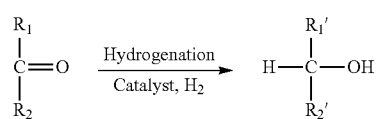

wherein $R_1$ and $R_2$ are the same or different, when $R_1$ is alkyl $R_1'=R_1$, when $R_2$ is alkyl $R_2'=R_2$, when $R_1$ is alkenyl $R_1'$ is alkyl or alkenyl, when $R_2$ is alkenyl $R_2'$ is alkyl or alkenyl, $R_1$ and $R_1'$ have an equal number of carbon atoms, and $R_2$ and $R_2'$ have an equal number of carbon atoms. In an embodiment, $R_1'$ and $R_2'$ may be independently selected from the group consisting of $C_5$-$C_{21}$ linear or branched alkyl and $C_5$-$C_{21}$ linear or branched alkenyl.

Catalysts and conditions for fatty acid ketonization and long chain ketone selective hydrogenation are described, e.g., hereinabove. In an embodiment, the at least one fatty acid for the ketonization reaction (Scheme 1, supra) may comprise a mixture of at least two (2) fatty acids, and the long chain ether (e.g., as represented by general Formula I, infra) may comprise a mixture of at least three (3) long chain ethers. In an embodiment, a long chain ether prepared as disclosed herein may be in the range from $C_{26}$-$C_{86}$, or from $C_{35}$-$C_{86}$, or from $C_{35}$-$C_{70}$. The long chain secondary alcohol formed as described above is subsequently used for the synthesis of a long chain ether.

In an embodiment, the long chain secondary alcohol, or a long chain alkoxide corresponding to the long chain secondary alcohol, may be reacted with an alkyl halide to form a long chain ether according to the following Scheme 6:

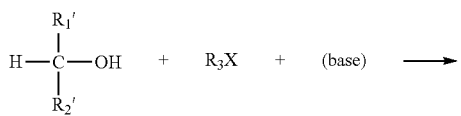

-continued

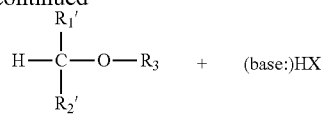 + (base:)HX wherein $R_1'$ and $R_2'$ may be independently selected from $C_5$-$C_{21}$ linear or branched alkyl and $C_5$-$C_{21}$ linear or branched alkenyl, wherein $R_3$ is selected from $C_1$-$C_3$ alkyl, $C_4$-$C_{22}$ linear or branched alkyl, $C_2$-$C_3$ alkenyl, and $C_4$-$C_{22}$ linear or branched alkenyl, and X is a halogen atom. In an embodiment, the reaction of the long chain secondary alcohol, or the corresponding alkoxide, with the alkyl halide may be performed in the presence of a base. Alkoxides may also be referred to herein as an alcoholate, an alcoholate salt or an alcoholate anion.

In an embodiment, such process may comprise converting (deprotonating) the long chain secondary alcohol (e.g., Scheme 6) to the corresponding long chain alkoxide; and thereafter the long chain alkoxide may be reacted with the alkyl halide, e.g., essentially according to Scheme 6. In an embodiment, the corresponding long chain alkoxide may be in the form of an alkali metal alcoholate. In an embodiment, the deprotonation reaction to produce the alkali metal alcoholate from the corresponding alcohol may be performed either by reacting the alcohol with a strong base, such as sodium hydride or sodium isopropoxide or potassium tert-butoxide, or with an alkali metal, such as sodium or potassium. In another embodiment, an alkoxide may be generated electrolytically from the corresponding alcohol as described hereinbelow.

In an embodiment, a long chain ether prepared according to Scheme 6 may be in the range from $C_{26}$-$C_{86}$, or from $C_{35}$-$C_{86}$, or from $C_{35}$-$C_{70}$. In an embodiment, a long chain ether product prepared according to processes as disclosed herein may comprise a mixture of two or more long chain ethers.

According to a further embodiment of a process for preparing a long chain ether from a first long chain secondary alcohol, the first long chain secondary alcohol may itself be prepared from a long chain ketone, wherein the long chain ketone may be prepared e.g., as described hereinabove according to Scheme 1, supra, and the long chain ketone may be contacted with a selective ketone hydrogenation catalyst under selective ketone hydrogenation conditions to provide the first long chain secondary alcohol, e.g., as described hereinabove according to Scheme 2, supra. Thereafter, the first long chain secondary alcohol may be reacted with a halogenating agent to form a halide derivative of the first long chain secondary alcohol; and the halide derivative of the first long chain secondary alcohol may be reacted with a second alcohol, or with an alkoxide corresponding to the second alcohol, to form a long chain ether according to the following Scheme 7:

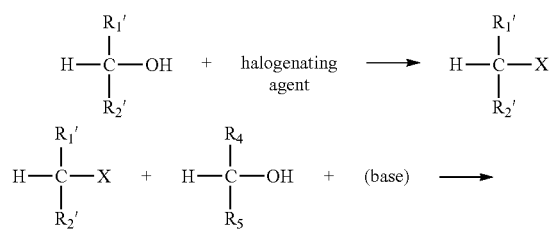

-continued

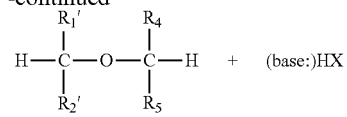 + (base:)HX wherein $R_1'$ and $R_2'$ may be independently selected from $C_5$-$C_{21}$ linear or branched alkyl and $C_5$-$C_{21}$ linear or branched alkenyl, wherein $R_4$ and $R_5$ are independently selected from $C_1$-$C_3$ alkyl, $C_4$-$C_{21}$ linear or branched alkyl, $C_2$-$C_3$ alkenyl, and $C_4$-$C_{21}$ linear or branched alkenyl. As disclosed herein, various methods may be used to convert an alcohol to the corresponding alkoxide. In an embodiment, an alkoxide corresponding to the second alcohol may be generated electrolytically.

Non-limiting examples of halogenating agents for forming the halide derivative of the long chain secondary alcohol include hydrogen halide, HX, wherein X is selected from Cl, Br, and I) and thionyl halide, $SOX_2$, wherein X is selected from Cl and Br. The halogenation may be performed in the absence of a catalyst or in the presence of a catalyst. For thionyl halide, such catalyst may be a weak base such as pyridine. For the HX addition, anhydrous $ZnX_2$ or $CaX_2$ will in some cases promote the replacement of the alcohol group with the halide.

In an embodiment, the halide derivative of the first long chain secondary alcohol may be reacted with the alkoxide corresponding to the second alcohol. In an embodiment, the second alcohol may be a short chain alcohol, such as isopropanol. In another embodiment, the second alcohol may comprise a second long chain secondary alcohol. In a sub-embodiment, the second long chain secondary alcohol may be prepared according to Schemes 1 and 2, supra. In an embodiment, long chain ether products prepared according to Scheme 7 may be in the bright stock range. In an embodiment, long chain ethers prepared as disclosed herein may be in the range from $C_{26}$-$C_{86}$, or from $C_{35}$-$C_{86}$, or from $C_{35}$-$C_{70}$.

As noted hereinabove, in an embodiment a long chain ether may be prepared by reacting a long chain alkoxide with an alkyl halide. As further noted hereinabove, in another embodiment a long chain ether may also be prepared by reacting a first long chain secondary alcohol with a halogenating agent to form a halide derivative of the first long chain secondary alcohol, and thereafter reacting the halide derivative with an alkoxide. In an embodiment, such alkoxides may be generated electrolytically from the corresponding alcohol, wherein the alcohol may be, e.g., a long chain alcohol, a light (volatile) alcohol, a secondary alcohol, or a primary alcohol, and the like. A long chain alkoxide, e.g., for producing a long chain ether, may be prepared either: i) directly by feeding a long chain alcohol to a suitable electrolytic cell for conversion of the alcohol to the corresponding long chain alkoxide, or ii) indirectly by reacting a long chain alcohol with an electrolytically generated light alkoxide corresponding to a volatile alcohol.

Electrolytic Generation of Alkoxides

FIG. 1 schematically represents an electrolytic cell and process for electrolytically generating an alkoxide from an alcohol. With further reference to FIG. 1, electrolytic cell 100 may include a vessel 5 housing an anolyte chamber 10 (hereinafter anolyte 10).

Electrolytic cell 100 may further include an anode 12 disposed in anolyte 10, an anolyte inlet 14 to anolyte 10, and an anolyte outlet 16 from anolyte 10. Electrolytic cell 100 may further include a catholyte chamber 20 (hereinafter catholyte 20). Electrolytic cell 100 may still further include a cathode 22 disposed in catholyte 20, a catholyte inlet 24 to catholyte 20, and a catholyte outlet 26 from catholyte 20.

Electrolytic cell 100 may still further include a selectively permeable membrane 15. Membrane 15 may be disposed between anolyte 10 and catholyte 20 to define separate anolyte and catholyte chambers, 10 and 20 respectively, of cell 100. In an embodiment, membrane 15 may be an ion conducting membrane. In an embodiment, membrane 15 may be selectively permeable to alkali metal ions, such as Na ions. In an embodiment, membrane 15 may be at least substantially impermeable to other materials present in anolyte 10 and catholyte 20. Various materials are known in the art to exhibit selective permeability to Na+ or other alkali metal ions. In an embodiment, membrane 15 may comprise a ceramic sodium ion conductor. In an embodiment, membrane 15 may comprise a NaSICON (Na Super Ion CONducting) type material (see, e.g., N. Anantharamulu, et al., J. Mater. Sci. (2011) 46:2821-2837). A non-limiting example of a material for membrane 15 is sodium ionic conductors of the general formula $Na_{1+x}Zr_2Si_xP_{3-x}O_{12}$, wherein $0 \leq x \leq 3$, or $(Na_5(Rare Earth)Si_4O_{12})_{1-\delta}(Rare Earth)_2Si_2O_{10})_\delta$, wherein Rare Earth is Nd, Dy or Sm, and $\delta$ is a measure of sodium deficiency in the ceramic membrane.

Liquid(s), e.g., electrolyte solution(s) and the like, may be introduced to and removed from anolyte 10 via anolyte inlet 14 and anolyte outlet 16, respectively. Similarly, electrolytes, substrates, solvents, or the like may be introduced to and removed from catholyte 20 via catholyte inlet 24 and catholyte outlet 26, respectively. Gases, such as hydrogen and oxygen, that may be evolved during operation of cell 100 may be removed from cell 100, e.g., via vents (not shown).

Although the operation of cell 100 will be described primarily with respect to the use of NaOH solution as electrolyte within anolyte 10, it is to be understood that other inorganic sodium salts and other alkali metal salts may also be applicable to the electrolytic generation of various alkoxides. Electrolytic cell 100 and its components are not limited to any particular configuration or materials. Suitable electrically conductive materials that may be used for anode 12 and cathode 22 include materials such as for instance nickel, cobalt, iron, platinum, various alloys, carbon/graphite and combination thereof.

During operation of cell 100, a solution of NaOH may be introduced into anolyte 10 of electrolytic cell 100 via anolyte inlet 14. Na ions migrate through membrane 15 from anolyte 10 to catholyte 20 under the influence of an electric potential applied between to cathode 22 and anode 12. At the same time, an alcohol substrate (represented as ROH) may be introduced into catholyte 20 via catholyte inlet 24. At the cathode the alcohol reacts with electrons to form hydrogen and alcoholate anions, $RO^-$. In catholyte 20, Na+ ions combines with the alcoholate anions to form Na alkoxide, which may be represented generically as NaOR. Within anolyte 10, OH− ions are oxidized at anode 12 to produce oxygen and $H_2O$. In an embodiment, the concentration of $Na^+$ ions in anolyte 10 may be maintained in a desired range by introducing fresh NaOH to anolyte 10 via anolyte inlet 14 and by removing diluted NaOH solution from anolyte 10 via anolyte outlet 16. The electrolytically generated sodium alkoxide (NaOR) may be withdrawn from catholyte 20 via catholyte outlet 26. Cell 100 may be operated in continuous mode or batch mode for the electrolytic generation of various alkoxides, including long chain alkoxides and light alkoxides.

Electrolytic generation of an alkoxide from a corresponding alcohol is not limited to any particular type of alcohol substrates. In FIG. 1 and the description thereof, ROH represents an alcohol in a generic sense. As a non-limiting example, the feed, ROH, to catholyte 20 may be a long chain alcohol, a short chain alcohol, a primary alcohol, or a secondary alcohol, and the like. A short chain alcohol may also be referred to herein as a light alcohol or a volatile alcohol.

The electrolytic generation of an alkoxide, represented as MOR, from the corresponding alcohol, ROH, may be represented according to the following Scheme 9:

$$2MOH + 2ROH \rightarrow 2MOR + H_2 + \tfrac{1}{2}O_2 + H_2O$$

wherein M is an alkali metal.

In an embodiment, the alcohol feed, ROH, to electrolytic cell 100 may comprise a long chain secondary alcohol, wherein the long chain secondary alcohol may be represented as $R_1'CH(OH)R_2'$. As an example, a long chain alkoxide may be electrolytically generated from the corresponding long chain secondary alcohol according to the following Scheme 9A:

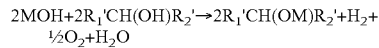
$$2MOH + 2R_1'CH(OH)R_2' \rightarrow 2R_1'CH(OM)R_2' + H_2 + \tfrac{1}{2}O_2 + H_2O$$

wherein $R_1'$ and $R_2'$ are independently selected from $C_5$-$C_{21}$ linear or branched alkyl and $C_5$-$C_{21}$ linear or branched alkenyl. In an embodiment, such long chain secondary alcohol may be produced from fatty acids, for example, via fatty acid ketonization and selective ketone hydrogenation as described hereinabove (see, e.g., Schemes 1 and 2, supra). In an embodiment, such long chain secondary alcohols may typically comprise from 11 to 43 carbon atoms.

In another embodiment the alcohol feed, ROH, to electrolytic cell 100 may comprise a $C_1$-$C_{22}$ primary alcohol. In another embodiment, the alcohol feed, ROH, to electrolytic cell 100 may comprise a volatile alcohol, e.g., in the range from $C_1$-$C_5$, to yield a light alkoxide, wherein the light alkoxide may be represented generically as MOR, wherein M represents an alkali metal and R represents a $C_1$-$C_5$ linear or branched alkyl group.

In an embodiment, the light alkoxide may be reacted with a long chain alcohol to provide the corresponding long chain alkoxide and the volatile alcohol corresponding to the light alkoxide, e.g., according to the following Scheme 10:

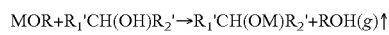
$$MOR + R_1'CH(OH)R_2' \rightarrow R_1'CH(OM)R_2' + ROH(g) \uparrow$$

wherein MOR represents the light alkoxide, and ROH represents the volatile alcohol, wherein the latter may be evaporated to leave the long chain alkoxide. In an embodiment, R may be selected from a $C_1$-$C_5$ linear or branched alkyl group, or a $C_2$-$C_5$ linear or branched alkyl group, or a $C_3$-$C_4$ linear or branched alkyl group. In a sub-embodiment, R may be selected from isopropyl and tert-butyl.

In a sub-embodiment, the alcohol feed, ROH, to electrolytic cell 100 may comprise a volatile alcohol, such as isopropanol or tert-butanol. As a non-limiting example, an isopropanol feed to electrolytic cell 100 may yield sodium isopropanolate according to the following Scheme 9B:

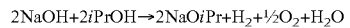
$$2NaOH + 2iPrOH \rightarrow 2NaOiPr + H_2 + \tfrac{1}{2}O_2 + H_2O$$

The sodium isopropanolate may then be reacted with a long chain alcohol to provide the corresponding long chain alkoxide and isopropanol, e.g., according to the following Scheme 10A:

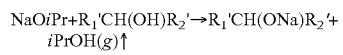
$$NaOiPr + R_1'CH(OH)R_2' \rightarrow R_1'CH(ONa)R_2' + iPrOH(g) \uparrow$$

wherein the isopropanol may be evaporated to yield the long chain alkoxide.

In an embodiment, a long chain alkoxide may be reacted with an alkylating agent to form a long chain ether, e.g., according to the following Scheme 8:

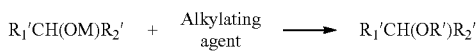

wherein M is an alkali metal, and R' is selected from the group consisting of $C_1$-$C_3$ alkyl, $C_4$-$C_{22}$ linear or branched alkyl, $C_2$-$C_3$ alkenyl, and $C_4$-$C_{22}$ linear or branched alkenyl. The alkylating agent may be any agent capable of transferring the alkyl group, R', to the alcoholate oxygen. In an embodiment, the alkylating agent may be an alkyl halide, and a long chain alkoxide may be reacted with the alkyl halide to form a long chain ether, e.g., according to the following Scheme 8A:

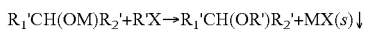

wherein R'X represents the alkyl halide, R' may be selected from $C_1$-$C_3$ alkyl, $C_4$-$C_{22}$ linear or branched alkyl, $C_2$-$C_3$ alkenyl, and $C_4$-$C_{22}$ linear or branched alkenyl, and X is a halogen atom. In an embodiment, M is Na and X is selected from Cl, Br, and I. In another embodiment, the alkylating agent may be selected from triflate, a perfluoroalkylsulfonate, an alkylsulfonate ester, and a sulfate ester or sulfate diester.

In another embodiment, a halide derivative of a first long chain secondary alcohol may be produced by reacting the long chain secondary alcohol with a halogenating agent, e.g., according to Scheme 7A:

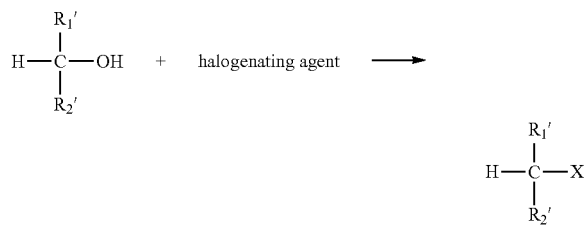

wherein X is a halogen atom. A second alcohol, such as a second long chain secondary alcohol, may be converted to an alkoxide corresponding to the second alcohol, and the alkoxide may be reacted with the halide derivative to provide a long chain ether, e.g., according to the following Scheme 7B:

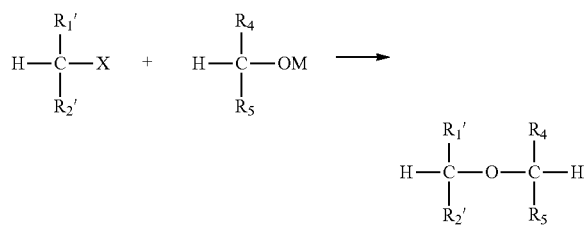

wherein M is an alkali metal, and $R_4$ and $R_5$ are independently selected from the group consisting of $C_1$-$C_3$ alkyl, $C_4$-$C_{21}$ linear or branched alkyl, $C_2$-$C_3$ alkenyl, and $C_4$-$C_{21}$ linear or branched alkenyl.

Thus, alkoxides may be generated, either directly or indirectly, by electrolytic methods; and such alkoxides may be useful in preparing long chain ethers from long chain secondary alcohols via a plurality of routes.

In an embodiment, the alcohol feed, ROH, may be anhydrous or at least substantially anhydrous. In an embodiment, electrolytic cell 100 may be operated at a temperature in the range from ambient temperature to 100° C. Since the melting point of the alkoxides (or alcoholate salts) corresponding to $C_{11}$-$C_{43}$ secondary alcohols are typically below (<) 100° C., in an embodiment catholyte 20 may be solvent free, e.g., in an embodiment a substrate feed to catholyte 20 may comprise neat alcohol (ROH). In another embodiment, the alcohol feed, ROH, to catholyte 20 may include a suitable solvent. In an embodiment, the alcohol feed, ROH, to catholyte 20 may comprise a mixture of secondary alcohols. Such a mixture of secondary alcohols may be obtained, e.g., from ketonization of a mixture of two or more fatty acids followed by selective hydrogenation of the resulting mixture of long chain ketones. In an embodiment, a solvent for an alcohol substrate, ROH, being fed to catholyte 20 may comprise one or more lighter alcohols.

In an embodiment, the electrical conductivity of the catholyte solution, e.g., a sodium alkoxide/alcohol mixture, may be increased by the addition to catholyte 20 of a suitable supporting electrolyte. As a non-limiting example, such a supporting electrolyte may comprise a low melting salt, such as a polyalkyl ammonium salt, a pyridinium salt, or an imidazolium salt.

Distilling

In an embodiment, a step of distilling may employ one or more distillation columns to separate the desired product(s) from by-products. In an embodiment, the step of distilling may employ flash distillation or partial condensation techniques to remove by-products including at least low molecular weight materials. Those of skill in the art will recognize that there is some flexibility in characterizing the high and low boiling fractions, and that the products may be obtained from "cuts" at various temperature ranges.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed. Additionally, chemical species including reactants and products designated by a numerical range of carbon atoms include any one or more of, or any combination of, or all of the chemical species within that range.

Any term, abbreviation or shorthand not defined is understood to have the ordinary meaning used by a person skilled in the art at the time the application is filed. The singular forms "a," "an," and "the," include plural references unless expressly and unequivocally limited to one instance. All publications, patents, and patent applications cited in this application are incorporated by reference herein in their entirety to the extent not inconsistent herewith.

Modifications of the exemplary embodiments disclosed above may be apparent to those skilled in the art in light of this disclosure. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

What is claimed is:

1. A process, comprising:

a) providing a long chain secondary alcohol having the following general Formula I:

$$R_1'CH(OH)R_2' \qquad \mathrm{I}$$

wherein $R_1'$ and $R_2'$ are independently selected from the group consisting of $C_5$-$C_{21}$ linear or branched alkyl and $C_5$-$C_{21}$ linear or branched alkenyl;

b) converting the long chain secondary alcohol to a long chain alkoxide corresponding to the long chain secondary alcohol; and c) reacting the long chain alkoxide with an alkylating agent to form a long chain ether according to the following Scheme 8:

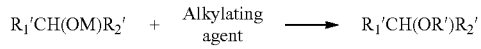

wherein:

M is an alkali metal, and

R' is selected from the group consisting of $C_1$-$C_3$ alkyl, $C_4$-$C_{22}$ linear or branched alkyl, $C_2$-$C_3$ alkenyl, and $C_4$-$C_{22}$ linear or branched alkenyl.

2. The process according to claim 1, wherein step b) comprises electrolytically generating the long chain alkoxide from the long chain secondary alcohol.

3. The process according to claim 1, wherein step b) comprises:

d) providing a light alkoxide; and e) reacting the light alkoxide with the long chain secondary alcohol to form the long chain alkoxide corresponding to the long chain secondary alcohol according to the following Scheme 10:

$$MOR + R_1'CH(OH)R_2' \rightarrow R_1'CH(OM)R_2' + ROH(g)\uparrow$$

wherein:

MOR represents the light alkoxide, and

R is selected from the group consisting of $C_1$-$C_5$ linear or branched alkyl.

4. The process according to claim 3, wherein step d) comprises electrolytically generating the light alkoxide from a volatile alcohol.

5. The process according to claim 4, wherein the volatile alcohol is selected from the group consisting of isopropanol and tert-butanol.

6. The process according to claim 1, wherein step c) comprises reacting the long chain alkoxide with an alkyl halide to form the long chain ether according to the following Scheme 8A:

$$R_1'CH(OM)R_2' + R'X \rightarrow R_1'CH(OR')R_2' + MX(s)\downarrow$$

wherein R'X represents the alkyl halide, R' is as defined in claim 1, and X is a halogen atom.

7. The process according to claim 1, wherein step a) comprises:

f) contacting at least one fatty acid with a ketonization catalyst in a ketonization zone under ketonization conditions to provide a long chain ketone according to the following Scheme 1:

$$R_1COOH + R_2COOH \rightarrow R_1C(O)R_2 + CO_2 + H_2O$$

wherein $R_1$ and $R_2$ are independently selected from the group consisting of $C_5$-$C_{21}$ linear or branched alkyl and $C_5$-$C_{21}$ linear or branched alkenyl; and g) contacting the long chain ketone with a selective ketone hydrogenation catalyst in a ketone hydrogenation zone in the presence of hydrogen gas under selective ketone hydrogenation conditions to provide the long chain secondary alcohol according to the following Scheme 2:

$$R_1C(O)R_2 + H_2 \rightarrow R_1'CH(OH)R_2'$$

wherein:

$R_1$ and $R_2$ are the same or different, when $R_1$ is alkyl $R_1' = R_1$, when $R_2$ is alkyl $R_2' = R_2$, when $R_1$ is alkenyl $R_1'$ is alkyl or alkenyl, when $R_2$ is alkenyl $R_2'$ is alkyl or alkenyl, $R_1$ and $R_1'$ have an equal number of carbon atoms, and $R_2$ and $R_2'$ have an equal number of carbon atoms, and wherein the long chain ether is in the range from $C_{26}$-$C_{86}$.

8. A process, comprising:

a) contacting at least one fatty acid with a ketonization catalyst in a ketonization zone under ketonization conditions to provide a long chain ketone according to the following Scheme 1:

$$R_1COOH + R_2COOH \rightarrow R_1C(O)R_2 + CO_2 + H_2O$$

wherein $R_1$ and $R_2$ are independently selected from the group consisting of $C_5$-$C_{21}$ linear or branched alkyl and $C_5$-$C_{21}$ linear or branched alkenyl;

b) contacting the long chain ketone with a selective ketone hydrogenation catalyst in a ketone hydrogenation zone in the presence of hydrogen gas under selective ketone hydrogenation conditions to provide a long chain secondary alcohol according to the following Scheme 2:

$$R_1C(O)R_2 + H_2 \rightarrow R_1'CH(OH)R_2'$$

wherein:

$R_1$ and $R_2$ are the same or different, when $R_1$ is alkyl $R_1' = R_1$, when $R_2$ is alkyl $R_2' = R_2$, when $R_1$ is alkenyl $R_1'$ is alkyl or alkenyl, when $R_2$ is alkenyl $R_2'$ is alkyl or alkenyl, $R_1$ and $R_1'$ have an equal number of carbon atoms, and $R_2$ and $R_2'$ have an equal number of carbon atoms;

c) converting the long chain secondary alcohol to a long chain alkoxide corresponding to the long chain secondary alcohol; and d) reacting the long chain alkoxide with an alkylating agent to form a long chain ether according to the following Scheme 8:

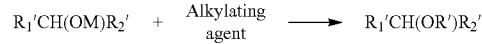

wherein M is an alkali metal, and R' is selected from the group consisting of $C_1$-$C_3$ alkyl, $C_4$-$C_{22}$ linear or branched alkyl, $C_2$-$C_3$ alkenyl, and $C_4$-$C_{22}$ linear or branched alkenyl.

9. The process according to claim 8, wherein step c) comprises electrolytically generating the long chain alkoxide from the long chain secondary alcohol.

10. The process according to claim 8, wherein step c) comprises reacting a light alkoxide with the long chain secondary alcohol to form the long chain alkoxide corresponding to the long chain secondary alcohol according to the following Scheme 10:

$$MOR + R_1'CH(OH)R_2' \rightarrow R_1'CH(OM)R_2' + ROH(g)\uparrow$$

wherein MOR represents the light alkoxide, and R is selected from the group consisting of $C_1$-$C_5$ linear or branched alkyl.

11. The process according to claim 10, wherein the light alkoxide is electrolytically generated from a volatile alcohol.

12. The process according to claim 10, wherein R is selected from the group consisting of isopropyl and tert-butyl.

13. The process according to claim 8, wherein:
the alkylating agent comprises an alkyl halide, and
step d) comprises reacting the long chain alkoxide with the alkylating agent to form the long chain ether according to the following Scheme 8A:

$$R_1'CH(OM)R_2' + R'X \rightarrow R_1'CH(OR')R_2' + MX(s)\downarrow$$

wherein R'X represents the alkyl halide, R' is as defined in claim 8, and X is a halogen atom.

14. The process according to claim 8, wherein:
$R_1^1$, and $R_2'$ are independently selected from the group consisting of $C_5$-$C_{21}$ linear or branched alkyl, and
the long chain ether is in the range from $C_{26}$-$C_{86}$.

15. A process, comprising:
a) contacting at least one fatty acid with a ketonization catalyst in a ketonization zone under ketonization conditions to provide a long chain ketone according to the following Scheme 1:

$$R_1COOH + R_2COOH \rightarrow R_1C(O)R_2 + CO_2 + H_2O$$

wherein $R_1$ and $R_2$ are independently selected from the group consisting of $C_5$-$C_{21}$ linear or branched alkyl and $C_5$-$C_{21}$ linear or branched alkenyl;

b) contacting the long chain ketone with a selective ketone hydrogenation catalyst in a ketone hydrogenation zone in the presence of hydrogen gas under selective ketone hydrogenation conditions to provide a first long chain secondary alcohol according to the following Scheme 2:

$$R_1C(O)R_2 + H_2 \rightarrow R_1'CH(OH)R_2'$$

wherein:
$R_1$ and $R_2$ are the same or different,
when $R_1$ is alkyl $R_1'$=$R_1$,
when $R_2$ is alkyl $R_2'$=$R_2$,
when $R_1$ is alkenyl $R_1'$ is alkyl or alkenyl,
when $R_2$ is alkenyl $R_2'$ is alkyl or alkenyl,
$R_1$ and $R_1'$ have an equal number of carbon atoms, and
$R_2$ and $R_2'$ have an equal number of carbon atoms;

c) reacting the first long chain secondary alcohol with a halogenating agent to form a halide derivative of the first long chain secondary alcohol according to the following Scheme 7A:

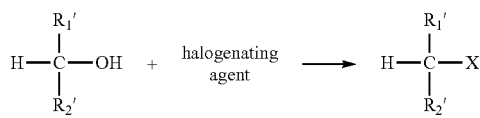

wherein X is a halogen atom;

d) providing a second alcohol;
e) converting the second alcohol to an alkoxide corresponding to the second alcohol; and
f) reacting the halide derivative of the first long chain secondary alcohol with the alkoxide to form a long chain ether.

16. The process according to claim 15, wherein step e) comprises electrolytically generating the alkoxide corresponding to the second alcohol.

17. The process according to claim 15, wherein:
the second alcohol comprises a second long chain secondary alcohol, and
step f) comprises reacting the halide derivative of the first long chain secondary alcohol with the alkoxide corresponding to the second alcohol to form the long chain ether according to the following Scheme 7B:

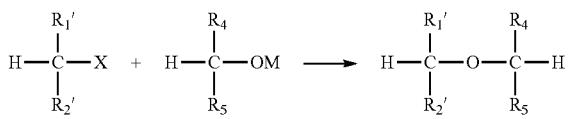

wherein M is an alkali metal, and $R_4$ and $R_5$ are independently selected from the group consisting of $C_1$-$C_3$ alkyl, $C_4$-$C_{21}$ linear or branched alkyl, $C_2$-$C_3$ alkenyl, and $C_4$-$C_{21}$ linear or branched alkenyl.

18. The process according to claim 15, wherein:
the second alcohol comprises a second long chain secondary alcohol, and
step e) comprises reacting a light alkoxide with the second alcohol to form the alkoxide corresponding to the second alcohol according to the following Scheme 10:

$$MOR + R_1'CH(OH)R_2' \rightarrow R_1'CH(OM)R_2' + ROH(g)\uparrow$$

wherein MOR represents the light alkoxide, M is an alkali metal, and R is selected from the group consisting of $C_1$-$C_5$ linear or branched alkyl.

19. The process according to claim 18, wherein the light alkoxide is electrolytically generated from a volatile alcohol.

20. The process according to claim 18, wherein R is selected from the group consisting of isopropyl and tert-butyl.

* * * * *